US012694994B2

(12) United States Patent
Siddiqi et al.

(10) Patent No.:     US 12,694,994 B2
(45) Date of Patent:         Jul. 28, 2026

(54) SYSTEMS, METHODS, AND DEVICES FOR MESSAGE CONTROL

(71) Applicant: Livemed Health Inc., Chicago, IL (US)

(72) Inventors: Saamer Siddiqi, Chicago, IL (US); Marc Anguiano, Chicago, IL (US)

(73) Assignee: Livemed Health Inc., Chicago, IL (US)

( * ) Notice: Subject to any disclaimer, the term of this patent is extended or adjusted under 35 U.S.C. 154(b) by 0 days.

(21) Appl. No.: 19/076,718

(22) Filed: Mar. 11, 2025

(65)                Prior Publication Data

US 2025/0285774 A1     Sep. 11, 2025

Related U.S. Application Data

(60) Provisional application No. 63/563,762, filed on Mar. 11, 2024.

(51) Int. Cl.
*G16H 80/00*        (2018.01)
*G06N 3/0499*       (2023.01)

(52) U.S. Cl.
CPC .......... *G16H 80/00* (2018.01); *G06N 3/0499* (2023.01)

(58) Field of Classification Search
CPC ....... G16H 80/00; G16H 10/60; G06N 3/0499
See application file for complete search history.

(56)                References Cited

U.S. PATENT DOCUMENTS

| | | | |
|---|---|---|---|
| 10,225,224 B1 * | 3/2019 | Reynolds | .............. H04L 51/224 |
| 2016/0026762 A1 * | 1/2016 | Radhakrishnan | ...... G16H 50/20 |
| | | | 705/3 |

| | | | |
|---|---|---|---|
| 2018/0276817 A1 * | 9/2018 | Isgum | ...................... G06T 7/10 |
| 2019/0139631 A1 | 5/2019 | Eshelman et al. | |
| 2019/0313230 A1 * | 10/2019 | MacGabann | ........... H04W 4/90 |

(Continued)

FOREIGN PATENT DOCUMENTS

| | | | | |
|---|---|---|---|---|
| WO | WO-2022006530 A1 * | 1/2022 | ....... G06F 16/90332 |
| WO | 2023049466 A2 | 3/2023 | |

OTHER PUBLICATIONS

Kontio et al., Predicting patient acuity from electronic patient records, Oct. 2014, Journal of Biomedical Informatics, vol. 51, pp. 35-40. (Year: 2014).*

(Continued)

*Primary Examiner* — Christopher L Gilligan
(74) *Attorney, Agent, or Firm* — Nelson Mullins Riley & Scarborough LLP

(57)                ABSTRACT

Systems, methods, and devices include a message control platform for use in a hospital, clinic, or other urgent setting. The message control platform includes a neural network which generates a supervised machine learning model with a message prioritization system and/or a recommendation generation system. The message control platform provides improved message control for communication devices used to manage patient workflow. A message control system includes input messages, received at a first computing device from a second computing device. The message prioritization system generates an acuity indicator corresponding to the patient-related data of the input message. The acuity indicator is presented with the one or more messages at a first user interface of the first computing device. Additionally, a recommendation output message, generated by the recommendation generation system, is presented at the first user interface of the first computing device.

16 Claims, 10 Drawing Sheets

(56) References Cited

U.S. PATENT DOCUMENTS

| 2020/0303074 | A1 | | 9/2020 | Mueller-Wolf | |
|---|---|---|---|---|---|
| 2021/0256701 | A1 | * | 8/2021 | Nozaki | G16H 50/20 |
| 2023/0048189 | A1 | | 2/2023 | Boddeti et al. | |
| 2024/0071618 | A1 | * | 2/2024 | Raheja | G16H 10/20 |
| 2024/0115196 | A1 | * | 4/2024 | Moshe | A61B 5/4552 |
| 2024/0172990 | A1 | * | 5/2024 | Mcgee | A61B 5/746 |
| 2024/0379239 | A1 | * | 11/2024 | Samset | G16H 50/30 |
| 2025/0046475 | A1 | * | 2/2025 | Shah | G06F 40/40 |
| 2025/0132036 | A1 | * | 4/2025 | Weston | G16H 10/20 |

OTHER PUBLICATIONS

International Search Report and Written Opinion issued in PCT/US2025/019397 on May 20, 2025, 16 pages.

* cited by examiner

100
302
110
120
118
9:41
9:41
Tuesday, 23 June
112 — Sarah RN (Boston Children's Hospi...
112 — Brian RN (Cleveland Clinic Hospital)
112 — Kaitlyn RN (Franco-USAese Hospit...
116
306
304
*FIG. 3A*

100

302

110

112

126

314

310

COMPUTING DEVICE(S) 402

PROCESSOR(S) 404

MEMORY DEVICE(S) 406

I/O PORT 408

COMMUNICATION PORT 410

403

405

407

130

100

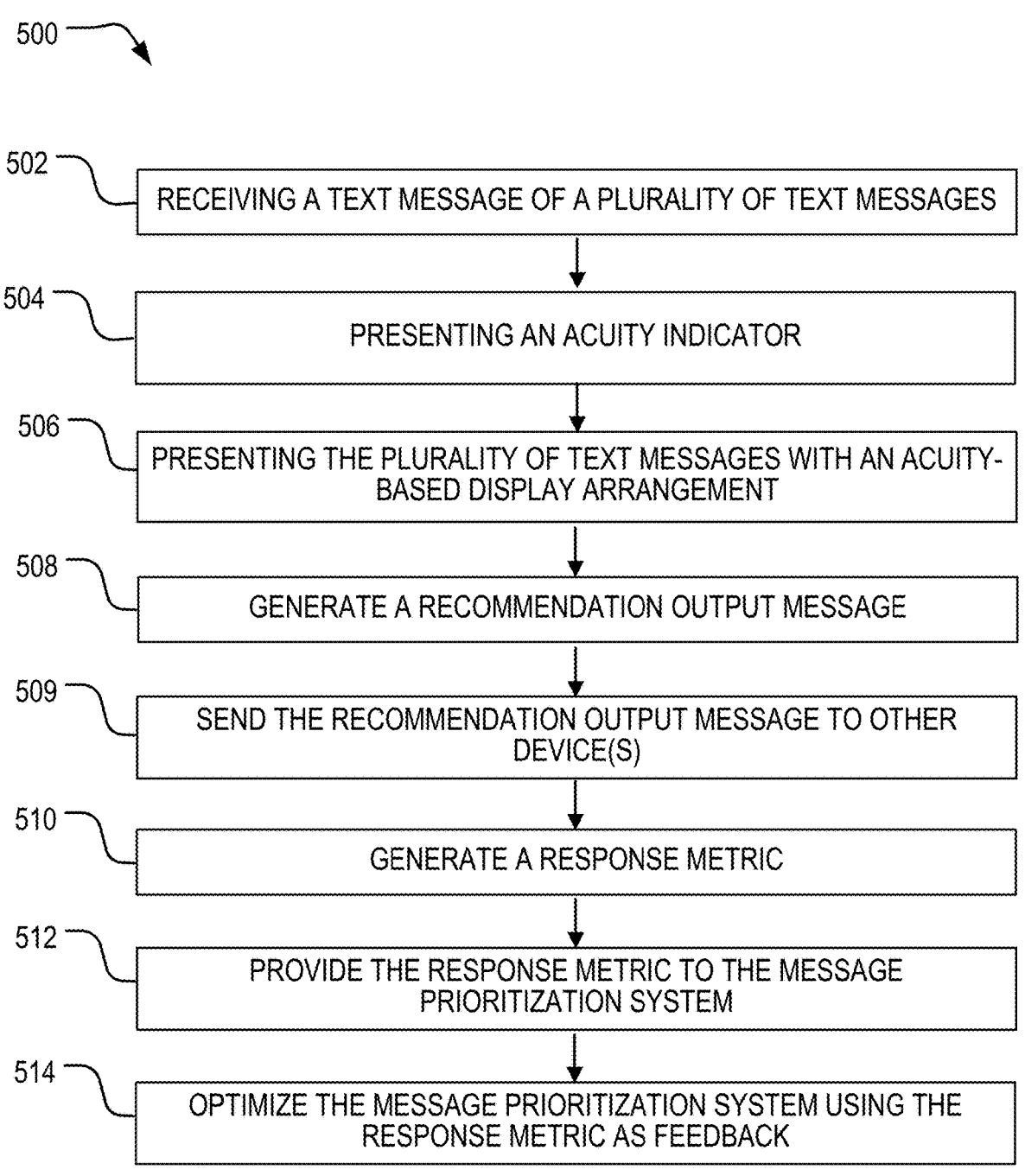

500

502 — RECEIVING A TEXT MESSAGE OF A PLURALITY OF TEXT MESSAGES

504 — PRESENTING AN ACUITY INDICATOR

506 — PRESENTING THE PLURALITY OF TEXT MESSAGES WITH AN ACUITY-BASED DISPLAY ARRANGEMENT

508 — GENERATE A RECOMMENDATION OUTPUT MESSAGE

509 — SEND THE RECOMMENDATION OUTPUT MESSAGE TO OTHER DEVICE(S)

510 — GENERATE A RESPONSE METRIC

512 — PROVIDE THE RESPONSE METRIC TO THE MESSAGE PRIORITIZATION SYSTEM

514 — OPTIMIZE THE MESSAGE PRIORITIZATION SYSTEM USING THE RESPONSE METRIC AS FEEDBACK

Figure 6:
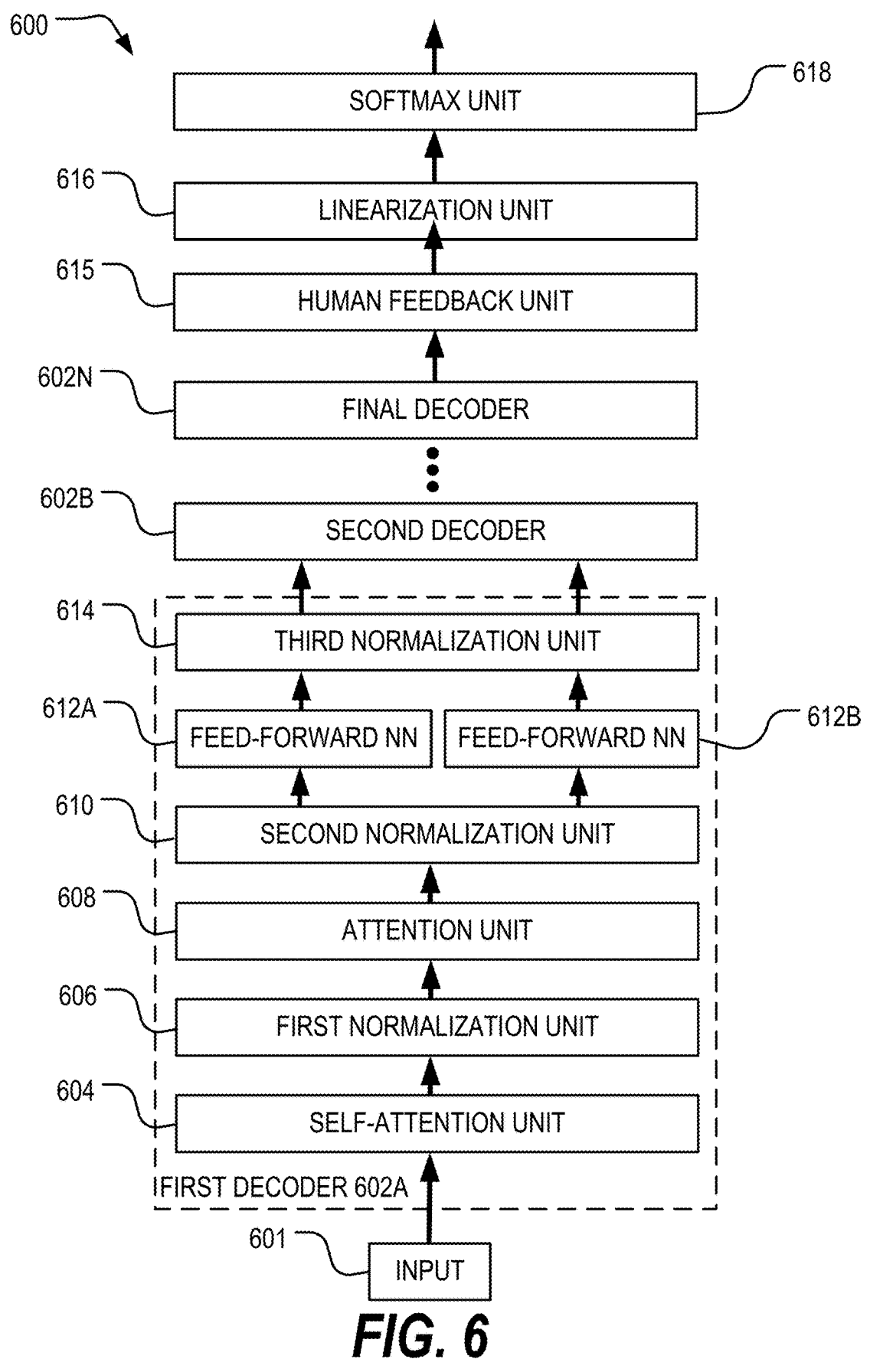

618 — SOFTMAX UNIT

616 — LINEARIZATION UNIT

615 — HUMAN FEEDBACK UNIT

602N — FINAL DECODER

602B — SECOND DECODER

614 — THIRD NORMALIZATION UNIT

612A — FEED-FORWARD NN     FEED-FORWARD NN — 612B

610 — SECOND NORMALIZATION UNIT

608 — ATTENTION UNIT

606 — FIRST NORMALIZATION UNIT

604 — SELF-ATTENTION UNIT

FIRST DECODER 602A

601 — INPUT

702N — FINAL ENCODER

702B — SECOND ENCODER

710 — SECOND NORMALIZATION UNIT

708A — FEED FORWARD NEURAL NETWORK     FEED FORWARD NEURAL NETWORK — 708B

706 — FIRST NORMALIZATION UNIT

704 — SELF-ATTENTION UNIT

FIRST ENCODER 702A

701 — INPUT

SYSTEMS, METHODS, AND DEVICES FOR MESSAGE CONTROL

CROSS-REFERENCE TO RELATED APPLICATION(S)

This application claims priority to U.S. Provisional Patent Application No. 63/563,762, filed on Mar. 11, 2024, entitled "Systems, Methods, and Devices for Message Control," which is hereby incorporated by reference in its entirety.

FIELD

Embodiments relate generally to systems, methods, and devices for message control to manage patient workflow.

BACKGROUND

Hospitals, clinics, and other care facilities rely on many devices and systems to manage patient workflow. However, patient management is often difficult, with multiple issues arising around the same time for different patients under care by many different people. Furthermore, the issues that patients are dealing with are often urgent, adding further difficulties.

It is with these observations in mind, among others, that various aspects of the presently disclosed technology were conceived and developed.

BRIEF SUMMARY

The systems, methods, and devices disclosed herein address some or all of the aforementioned issues. Various embodiments described herein may provide systems that parse through large amounts of data to present material to users on a user-friendly interface. The most important messages may be presented in a more prominent manner, while other messages of lower importance may be presented in a less prominent manner. For example, messages may be presented in a particular order on a user interface, with a particular color scheme which corresponds to a classification for a message. This may enable healthcare professionals and others to focus their energy on the most important and/or the most urgent tasks to ensure that they are using their time efficiently.

In some embodiments, models such as machine learning models (e.g., deep learning models) may be used to analyze messages and determine acuity levels for messages, thereby allowing the most important messages to be presented to users with increased prominence. However, models may also be used for other purposes.

Machine learning models may be formed using a decoder-only architecture where the architecture does not include any encoders. The decoder-only architecture may be beneficial to efficiently form models, and decoder-only architectures may be more scalable in some embodiments. The architectural complexity of decoder-only architectures may be reduced as decoder-only architectures do not rely on encoders. In some embodiments, models may be trained using both encoders and decoders, but the models may only use decoders when in production.

A decoder-only architecture may be used in order to allow for a variety of different use cases. For example, while other types of architectures may be less effective with limited amounts of training data, decoder-only architectures may be useful where a limited amount of training data is available. This may make decoder-only architectures particularly useful for different use cases ranging from use cases involving well known issues to other use cases involving rare or outlier issues. By contrast, other architectures such as encoder-only architectures are often dependent on large labeled datasets, limiting their potential.

Decoder-only models may be particularly beneficial in the healthcare context, where limited data may be available for different issues. These issues with limited data are further compounded by the uniqueness of issues faced by particular patients. For example, a given patient may have a particular issue that is very rare, or the patient may have a unique combination of medical issues that makes his or her issue rare. Given the rarity of a particular situation with a patient, less data may be available regarding situations with other patients that are comparable. Thus, the ability to make accurate predictions in this situation using a decoder-only model is particularly beneficial. However, decoder-only models may also be beneficial for use in other situations where the amount of data that is available is not so limited.

Decoder-only architectures may also use autoregressive generation, enabling inferences beyond a simple classification by generating structured outputs based on prior context. By using autoregressive generation, models may use the available context to make any outputs more accurate. By contrast, other architectures such as encoder-only architectures often lack autoregressive generation capabilities, limiting their potential. Decoder-only architectures may also be beneficial when used in handling natural language inputs from unstructured text (e.g., when care coordinators provide inputs such as consultation requests through typing or verbal inputs), and this may stem from the use of autoregressive generation. However, in other embodiments, models may be formed without using autoregressive generation.

Decoder-only architectures may continuously adapt to new information and any new context. The architectures may receive input material of various types to provide context that improves the accuracy of models. This may enhance any real-time decision support, and this may also ensure that models are more dynamic and personalized to a current condition for a patient. Models may be configured to output care suggestions based on patient-specific conditions, details within health records for a patient, prior interventions, and real-time monitoring data, but models may rely on other types of data.

Decoder-only architectures may also beneficially provide for flexible data utilization. Decoder-only architectures may have multimodal integration, allowing the architectures to process and generate content of various types (e.g., text, images, audio, video, etc.). With multimodal integration, decoder-only architectures may support structured data (e.g., EHR, lab results, vital signs, etc.) and unstructured data (clinical notes, physician consultations, video, unstructured text, etc.).

Decoder-only architectures may provide several other advantages. Decoder-only architectures may also be beneficial when working with diverse training datasets. Additionally, decoder-only architectures may include enhanced attention mechanisms that allow for rapid contextualization of common or trivial cases as well as rare or novel cases, thereby improving prediction of acuity levels and improving the accuracy of any output from a model. Attention mechanisms may be critical features within architectures. Attention mechanisms may be multi-headed attention mechanisms in some embodiments, and this may enable models to focus on different aspects of an input sequence simultaneously so that an improved contextual understanding may be provided. Multi-headed attention mechanisms may be beneficial to determine a base model that is used. The use of multi-headed attention mechanisms may further improve the quality of any models and any outputs from the models.

In various embodiments, architectures are described that are based on decoder-only transformers, and these may be optimized for healthcare applications in various ways. The architectures may provide domain-specific vocabulary integration, augmenting GPT models with medical terminology and healthcare specific language. Architectures may be configured to develop models with an enhanced contextual understanding by using domain-specific datasets that are relevant to different healthcare scenarios. In some embodiments, refinement of models may optionally be validated by healthcare professionals, subject matter experts, or others, providing a human-in-the-loop feedback approach. With this approach, the clinical accuracy and trustworthiness of any developed models may be enhanced. Generative adversarial network (GAN) may be implemented in some embodiments to facilitate human-in-the-loop feedback approaches, and this many enable models to quickly adapt to feedback from a human. Furthermore, architectures described herein may utilize prompt engineering to design and optimize input prompts to guide models, and this may result in an optimized input structuring for different inference tasks such as clinical summarization, recommendation generation, and other tasks.

Models that are developed may be fine-tuned using parameter efficient fine tuning (PEFT), which may include low-rank adaption (LoRA) or quantized low-rank adaption (qLoRA) techniques. These techniques may enhance a model's contextual understanding by incorporating domain-specific datasets that are relevant to various healthcare scenarios. LoRA adapters used for various inbound requests may be selected by agentic routing.

Training procedures can be used that cause any generated models to understand nuances of clinical urgency with high degrees of accuracy, with the model being tailored to the specific operational and clinical contexts faced by healthcare providers. This may be accomplished by obtaining relevant input data from various sources (e.g., medical research articles, general medical data regarding one or more conditions, treatments, dictionaries, etc.) to enable any models to have a better contextual understanding of medical issues.

Furthermore, any models that are developed may be continuously refined, enabling these models to stay up to date even with changes in context and changes in the environment, and reducing the costs required to update these models. Models may be configured to complete complicated determinations that even the most sophisticated users are incapable of completing, and models may identify patterns that even the most sophisticated users are incapable of identifying. In a triage situation where healthcare providers need to make quick decisions, various embodiments described herein may rapidly process data and update faster than humans can adapt, thereby allowing effective determinations to be made very rapidly.

Models may beneficially provide various outputs. For example, models may be used to predict acuity levels for different messages, such as those sent to a healthcare professional. In some embodiments, models may be used to review available patient data and/or other data and make determinations regarding the severity of a medical issue for a patient, a diagnosis of a medical issue for a patient, a treatment plan for the patient, whether a specialist consultation is necessary, etc. Where models determine that a specialist consultation is necessary, the models may be configured to suggest a particular specialist or a particular type of specialist that is needed. Models may also be configured to generate and output textual recommendations on how to proceed (e.g., with a diagnosis, an intervention, treatment plan, an indication of whether a specialist consultation, etc.).

Models may enhance interactions with patients by analyzing the available data and then generating additional clarifying questions based on the available data. This may provide healthcare providers with improved questions that they may optionally ask, which may lead to an improved quality of data so that healthcare providers may make more well-informed decisions. Models may perform complex analyses with such speed and efficiency and in such a rapid and timely manner that even the most experienced healthcare providers cannot provide, thereby allowing questions to be developed that the healthcare providers would not have thought of.

Techniques disclosed herein may optimize how messages are presented, thereby making computing devices easier to use and allowing them to be used more efficiently. As a result of this increased efficiency, computing devices may effectively be used while requiring less processing power. Additionally, the increased efficiency may reduce memory storage requirements as compared to techniques used by other messaging systems.

In an example embodiment, a message control system is provided including a message prioritization system. The message prioritization system includes one or more processors and one or more memory devices comprising computer readable code. The computer readable code is configured, when executed by the one or more processors, to cause the one or more processors to generate an acuity indicator corresponding to patient-related data from one or more messages received at a first computing device from a second computing device and also to cause the acuity indicator to be sent to the first computing device.

In some embodiments, the message control system may also include a processing unit having a machine-learning architecture. Additionally, in some embodiments, the machine-learning architecture may comprise one or more decoders, and the machine-learning architecture may be provided without any encoders. In some embodiments, the machine learning architecture may comprise a feed-forward neural network architecture comprising a transformer and a classifier. Furthermore, in some embodiments, the transformer and the classifier may be trained with training data including a plurality of training text messages including patient information. In some embodiments, the machine-learning architecture may use autoregressive generation.

In some embodiments, the message control system may also comprise the first computing device comprising a first user interface. The first computing device may be configured to present the acuity indicator with the one or more messages at the first user interface of the first computing device.

In some embodiments, the message control system may also comprise a recommendation generation system configured to generate a recommendation output message. Either the first computing device or the second computing device may be configured to present the recommendation output message.

In some embodiments, the first computing device may comprise computer readable code. The computer readable code of the first computing device may comprise an acuity-based push notification integration with the first computing device. When the computer readable code of the first computing device is executed, the acuity-based push notification integration may cause a determination a display order of the one or more messages at a display screen of the first computing device.

In some embodiments, the computer readable code may be configured, when executed by the one or more processors, to cause the one or more processors to receive a response metric and use the response metric as feedback to optimize the message prioritization system. The response metric may be based on activity at the first computing device responsive to the one or more messages. Furthermore, in some embodiments, the response metric may comprise one or more of a response content, a response time, an unaddressed message, or a subsequent action.

In some embodiments, the computer readable code may be configured, when executed by the one or more processors, to cause the one or more processors to assign a high-acuity classification to a first message of the one or more messages, to assign a medium-acuity classification or a low-acuity classification to a second message of the one or more messages, and to cause the first computing device to present an acuity-based display arrangement in which the first message is displayed with a higher presentation prominence than the second message. Furthermore, in some embodiments, the higher presentation prominence may comprise at least one of a higher position on a list, a font change, a larger font size, a screen portion designation, or a presentation color. Additionally, in some embodiments, the acuity indicator may be based on a color scheme which corresponds to a classification performed by the machine-learning message control platform.

In another example embodiment, a method of controlling messages with a machine-learning message control platform is provided. The method comprises receiving a text message of a plurality of text messages, with the text message including patient-related data. The method also comprises presenting an acuity indicator corresponding to the patient-related data to indicate an acuity classification of the patient-related data. Additionally, the method comprises presenting the plurality of text messages with an acuity-based display arrangement. The acuity-based display arrangement determines presentation prominence for the plurality of text messages using a plurality of acuity classifications.

In some embodiments, the method may also comprise generating a recommendation output message for presentation at a user interface of another computing device. In some embodiments, the method may also comprise generating a response metric by measuring a characteristic of an activity performed at the computing device responsive to the text message and also optimizing the machine-learning message control platform by providing the response metric as feedback to the message prioritization system.

In another example embodiment, a computing device for presentation of an acuity-based display arrangement is provided. The computing device comprises a display screen, one or more processors, and one or more memory devices comprising computer program code. The computer program code is configured, when executed by the one or more processors, to cause the one or more processors to perform various functions. These functions include receiving a text message of a plurality of text messages, with the text message including patient-related data. The functions also include causing presentation of an acuity indicator at the display screen, the acuity indicator corresponding to the patient-related data to indicate an acuity classification of the patient-related data. The functions also include causing presentation of the plurality of text messages with the acuity-based display arrangement at the display screen, with the acuity-based display arrangement describing presentation prominence for the plurality of text messages on the display screen using a plurality of acuity classifications generated by the message prioritization system of the machine-learning message control platform.

In some embodiments, the computer readable code may be configured, when executed by the one or more processors, to cause the one or more processors to generate a recommendation output message for presentation at a user interface of another computing device. Furthermore, in some embodiments, the recommendation output message may be generated using a recommendation generation system of the machine-learning message control platform. Additionally, in some embodiments, the computer readable code may be configured, when executed by the one or more processors, to cause the one or more processors to generate a response metric by measuring a characteristic of an activity performed at the computing device responsive to the text message and optimize the machine-learning message control platform by providing the response metric as feedback to the message prioritization system.

In another example embodiment, a message control system may be provided that includes one or more messages, received at a first computing device from a second computing device, including patient-related data. The message control system can also include an acuity indicator, generated by a message prioritization system of a message control platform, corresponding to the patient-related data. The acuity indicator can be presented with the one or more messages at a first user interface of the first computing device. Moreover, the message control system can include a recommendation output message, generated by a recommendation generation system of the message control platform, and presented at a second user interface of the second computing device.

In some embodiments, the message control platform may include at least an application stored and operating on the first computing device. The application can include an acuity-based push notification integration with the first computing device which determines a display order of the one or more messages at a display screen of the first computing device. Additionally, the message control platform can include a machine-learning, feed-forward neural network architecture using a transformer integrated with a classifier. The transformer and the classifier can be trained with training data including a plurality of training text messages including patient information. Moreover, the training data can be formed by manually labelling the plurality of training text messages with one or more training acuity labels. For instance, the one or more training acuity labels can include a high acuity label, a medium acuity label, and a low acuity label. Additionally, the training data can be formed by manually labelling the plurality of training text messages with training recommendation responses.

In some embodiments, the message control system may include a response metric, generated based on activity at the first computing device responsive to the one or more messages, provided to the message control system as continuous learning feedback for optimizing the message prioritization system or the recommendation generation system. The response metric can include one or more of a response content, a response time, an unaddressed message, or a subsequent action. The message control system can also include a first message of the one or more messages assigned to a high-acuity classification by the message prioritization system with a first timestamp; a second message of the one or more messages assigned to a medium-acuity classification or a low-acuity classification by the message prioritization system with a second timestamp, the second timestamp being after the first timestamp; and/or an acuity-based display arrangement in which the first message is displayed, at the first computing device, with a higher presentation prominence than the second message. Furthermore, the higher presentation prominence can include at least one of a higher position on a list, a font change, a larger font size, a screen portion designation, or a presentation color.

In some embodiments, a message control system may include an acuity indicator, generated by a message prioritization system of a machine-learning message control platform, the acuity indicator can correspond to patient-related data from a first message, and can be presented with the first message at a first user interface of a first computing device. The message control system can also include an acuity based display arrangement, on a display of the first computing device, in which the first message has a higher presentation prominence than a second message because the first message is associated, by the message prioritization system, with a higher acuity-based classification than the second message. Furthermore, the message control system can include a response metric corresponding to a user response to the first message or the second message, the response metric provided to the machine-learning message control platform to optimize a transformer or a classifier of the machine-learning message control platform.

In some embodiments, the message control system can include a recommendation output message, generated by a recommendation generation system of the machine-learning message control platform, and presented at a second user interface of a second computing device that generated the first message or the second message. Additionally, the first message can have a later timestamp than the second message. Moreover, the message control system can include an acuity-based push notification integration, by an application of the machine-learning message control platform executing on the first computing device, to control at least one of a display order of messages or a currently presented message. Furthermore, the acuity indicator can be based on a color scheme which corresponds to a classification performed by the machine-learning message control platform. For instance, the color scheme can include one or more of: a green color associated with a low-acuity classification; a yellow color or an orange color associated with a medium-acuity classification; or a red color associated with a high-acuity classification.

In some embodiments, a method of controlling messages with a machine-learning message control platform includes receiving, at a computing device, a text message of a plurality of text messages, the text message can include patient-related data; presenting, at a display screen of the computing device, an acuity indicator generated by a message prioritization system of the machine-learning message control platform, the acuity indicator can correspond to the patient-related data to indicate an acuity classification of the patient-related data; and/or presenting, at the display screen of the computing device, the plurality of text messages with an acuity-based display arrangement, the acuity-based display arrangement can determine presentation prominence for the plurality of text messages using a plurality of acuity classifications generated by the message prioritization system of the machine-learning message control platform.

In some embodiments, the method can also include generating a recommendation output message, using a recommendation generator system of the machine-learning message control platform, for presentation at a user interface of another computing device. Furthermore, the method can include generating a response metric by measuring a characteristic of an activity performed at the computing device responsive to the text message; and/or optimizing the machine-learning message control platform by providing the response metric as feedback to the message prioritization system.

The foregoing summary is intended to be illustrative and is not meant in a limiting sense. Many features of the examples may be employed with or without reference to other features of any of the examples. Additional aspects, advantages, and/or utilities of the presently disclosed technology will be set forth in part in the description that follows and, in part, will be apparent from the description, or may be learned by practice of the presently disclosed technology.

BRIEF DESCRIPTION OF THE DRAWINGS

The foregoing summary, as well as the following detailed description, will be better understood when read in conjunction with the appended drawings. For the purpose of illustration, there is shown in the drawings certain embodiments of the disclosed subject matter. It should be understood, however, that the disclosed subject matter is not limited to the precise implementations and features shown. The accompanying drawings, which are incorporated in and constitute a part of this specification, illustrate implementations of systems, methods, and devices consistent with the disclosed subject matter and, together with the description, serves to explain advantages and principles consistent with the disclosed subject matter, in which:

FIGS. 3A-3C illustrate a computing device with different graphical user interfaces (GUI)s, which can form at least a part of the system depicted in FIG. 1, in accordance with some embodiments discussed herein;

FIG. 5 illustrates an example method of machine-learning-based message control, which can be performed by any of the systems illustrated in FIGS. 1-4, in accordance with some embodiments discussed herein;

FIG. 6 illustrates an example system comprising a plurality of decoders that may be used to facilitate machine learning processes described herein, in accordance with some embodiments discussed herein;

DETAILED DESCRIPTION

Figure 1:
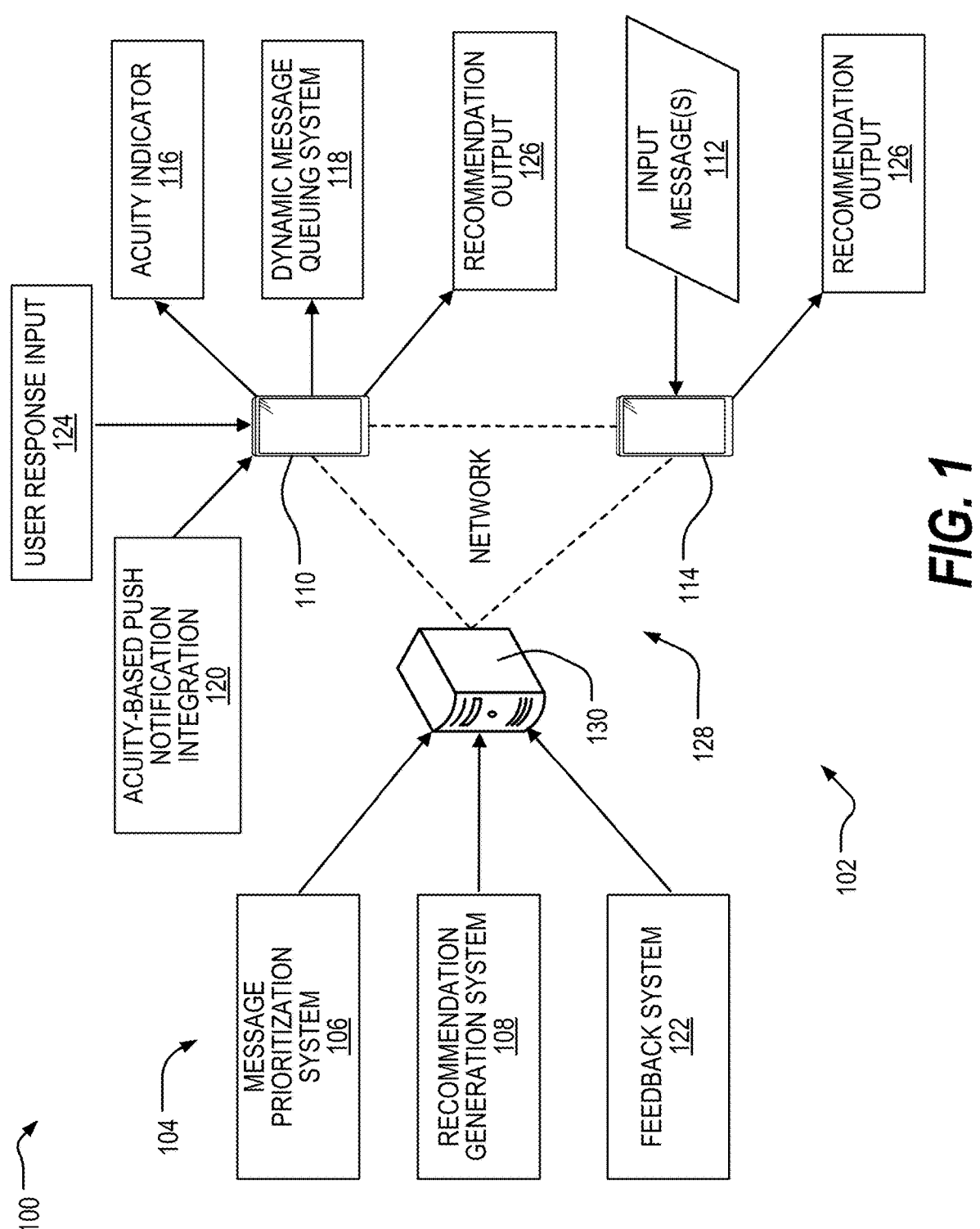
FIG. 1 illustrates an example system including a machine-learning message control platform, in accordance with some embodiments discussed herein.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other embodiments, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present technological concepts.

As used herein, a "unit", "system," or a "computing device" may optionally include one or more processors and one or more memory devices, with the memory device(s) comprising computer program code configured, when executed by the one or more processors, to cause the one or more processors to perform certain functions described herein. Other devices described herein may similarly possess processor(s) and memory device(s). However, a unit, system, computing device, and other devices described herein may possess other hardware components in other embodiments.

Systems, methods, and devices include a message control platform for use in a hospital, clinic, or other urgent setting to improve messaging interfaces involving patient workflow. The message control platform can include a supervised machine learning model using a feed-forward neural network trained to include a message prioritization system and/or a recommendation generation system. The message control system can analyze and augment input messages received at a first computing device from a second computing device. For instance, the message prioritization system can generate an acuity indicator corresponding to an acuity classification generated by the feed-forward neural network based on the patient-related information of the input message. The acuity indicator can be presented with the input message at a first user interface of the first computing device. Additionally, a recommendation output message can be generated by the recommendation generation system and can be presented at the first user interface of the first computing device or a second user interface of the second computing device.

As such, methods disclosed herein can prioritize clinical messages based on clinical acuity using specialized artificial intelligence (AI) algorithms uniquely trained on a niche-focused, custom-labelled dataset of clinical communications. This training procedure can cause the AI model to understand and interpret the nuances of clinical urgency with exceptional accuracy, tailored to the specific operational and clinical contexts of healthcare providers implementing the model. In some embodiments, the systems can also provide specialty suggestions to healthcare professionals, further leveraging the AI algorithms trained on the specialized training dataset. This training dataset can include detailed records of clinical communications, outcomes, and specialist feedback, such that the machine-learning model can generate new recommendations which are both precise and contextually relevant.

The systems disclosed herein can include a unified platform which merges real-time message prioritization with contextually relevant specialty recommendations, facilitated by AI algorithms trained on the exclusive, niche-focused training dataset. By customizing the training dataset for particular environments, the platform can provide highly relevant information for improving the messaging systems used by institutions. The platform can be provided to institutions, in some embodiments, as a Subscription-based Software as a service (SaaS). This approach can provide a streamlined and highly efficient decision-making process for healthcare providers, significantly reducing response times and improving patient care outcomes.

Additional advantages of the systems, methods, and devices discussed herein will become apparent from the detailed description below.

FIG. 1 illustrates an example system 100 including a message control platform 102 for use in a hospital, clinic, or other urgent setting. The message control platform 102 can include a neural network or other artificial intelligence-based system which generates a supervised machine learning model 104 with a message prioritization system 106 and/or recommendation generation system 108. These components of the message control platform 102 can provide improved message control for communication devices (e.g., a first computing device 110 and/or a second computing device 114) used to manage patient workflow.

For example, the second computing device 114 of the message control platform 102 can be used to draft one or more input message(s) 112. The second computing device 114 can be associated with a nurse, physician's assistant, doctor, or other clinical staff who prepares and send the input message(s) 112 to convey information related to a patient (e.g., a patient status, a change or update in patient status, a request for patient information, etc.) to the first computing device 110 associated with another person, such as a doctor, senior nurse, or other person supervising the nurse associated with the second computing device 114. It is to be understood that a plurality of computing devices may be used in a hospital setting to send many messages between doctors and nurses in a complex, urgent, real-time environment.

In some embodiments, the message prioritization system 106 can receive and assess the input message(s) 112 at the message prioritization system 106. The message prioritization system 106 can use machine-learning training of a feed-forward neural network architecture to generate an acuity prediction value for the input message(s) 112 based on the patient information conveyed in the input message(s) 112. As such, the input message(s) 112 can be presented at the receiving first computing device 110 with an acuity indicator 116 corresponding to the acuity prediction value. For instance, input message(s) 112 with a high probability prediction for a high acuity classification can be presented with a particular color indicating the high acuity classification, such as red. Additionally, input message(s) 112 with a high probability prediction for a medium acuity classification can be presented with a particular color indicating the medium acuity classification, such as yellow or orange. Moreover, input message(s) 112 with a high probability prediction for a low acuity classification can be presented with a particular color indicating the low acuity classification (e.g., green). In this way, the acuity indicator 116 can be at least partly based on a color scheme which includes different colors corresponding to different acuity classifications.

The acuity indicator 116 can also include a placement or position in a list of messages presented at the first computing device 110 such that certain high acuity messages have a higher display prominence than medium acuity messages and/or low acuity messages. For example, the message control platform 102 can include a dynamic message queuing system 118 which generates an acuity-based display arrangement for the input message(s) 112 at the first computing device 110 receiving the input message(s) 112. The acuity-based display arrangement can include a display order, such that an earlier received but higher acuity message is positioned above a more recent yet lower acuity message. Additionally or alternatively, the higher presentation prominence corresponding to higher acuity messages can include at least one of a more central position than other messages, a larger font than other messages, a different font than other messages, a particular display order, usage of a particular screen portion designation, a particular presentation color, playing a particular audio file or animation, triggering a haptic feedback feature of the first computing device 110, and/or combinations thereof. In some embodiments, the acuity based display arrangement can override a chronological arrangement of messages.

Furthermore, the message control platform 102 can include an application, operating on the first computing device 110 and/or the second computing device 114, which includes an acuity-based push notification integration 120 with the first computing device 110 and/or the second computing device 114. As such, the message control platform 102 can cause push notifications generated by an operating system (OS) of the first computing device 110 to have the acuity based display arrangement. As such, a display order of messages in different OS states (e.g., standby, sleep, idle, awake, etc.) can be determined by the different acuity classifications for the input message(s) 112. In some embodiments, input message(s) 112 having a highest acuity ranking is a currently presented message at the first computing device 110. In some embodiments, a first message having a first timestamp and a high acuity classification can be presented with a higher presentation prominence than a second message having a second timestamp and a lower acuity classification, even if the second timestamp is after and more recent than the first timestamp.

In some embodiments, the message control platform 102 further includes a feedback system 122 to provide continuous training to the supervised machine learning model 104. For instance, the message control platform 102 can measure and/or calculate different response metrics 228 from a user response input 124, at the first computing device 110, responsive to the input message(s) 112. The response metrics 228 are discussed in greater detail below regarding FIG. 2.

Moreover, the message control platform 102 can include the recommendation generation system 108 which creates a recommendation output 126 at the first computing device 110 and/or the second computing device 114. The recommendation output 126 can be generated based on the information conveyed in the input message(s) 112, such as patient information, request information, and so forth. The recommendation output 126 can provide a recommendation to the person receiving the input message(s) 112 and/or the person who drafted the input message(s) 112, with a recommendation for an additional action for that person to take.

Accordingly, in some embodiments, the message control platform 102 can provide an advanced notification system that employs artificial intelligence to send prioritized push notifications for urgent clinical messages, which can draw immediate attention from healthcare professionals. These notifications can be intelligently ranked based on the urgency derived from the message control platform's assessment of clinical data, user behavior, and the training dataset 220. Healthcare providers can use the message control platform 102 to receive alerts in real-time, tailored to their role and current context.

In some embodiments, the message control platform 102 can be deployed as an application stored and executing at the first computing device 110 and/or the second computing device 114 communicating via one or more network(s) 128. Additionally or alternatively, one or more server(s) 130, in some embodiments, can host at least some of the software components of the message control platform 102. In one implementation, the server(s) 130 also hosts a website or an application that users may visit to access the user interfaces (e.g., GUIs 302) discussed herein. The server(s) 130 may be one single server, a plurality of servers with each such server being a physical server or a virtual machine, or a collection of both physical servers and virtual machines. In another implementation, a cloud hosts one or more components of the message control platform 102. The message control platform 102, first computing device 110, the second computing device 114, the server(s) 130, and other resources connected to the network(s) 128 may access one or more additional servers for access to one or more websites, applications, web services interfaces. In some embodiments, models may be cloud-based, with devices relying on the cloud for artificial intelligence/machine learning processing. Access to the models may be provided through software as a service (SaaS) approaches.

The system 100 may also be connected to various sources so that input material may be obtained for the system 100. The system 100 may obtain consultation request data provided by the patient. These sources may be locations where patient-specific medical details are located, such as in an electronic health record. Patient-specific medical details may be included in structured or unstructured records in some embodiments. Input material may also be used to provide context to improve determinations. For example, input material may provide context regarding the language that is used in a particular area and/or the particular customs of a particular area, and this may be beneficial where the system is used in different countries. For example, input material may be provided related to census data, demographic information, healthcare provider facilities in the area, specialists for treating various conditions, availability of healthcare providers and/or workload, dictionaries, medical research articles, general medical data regarding one or more conditions, treatments, and for other issues.

Figure 2:
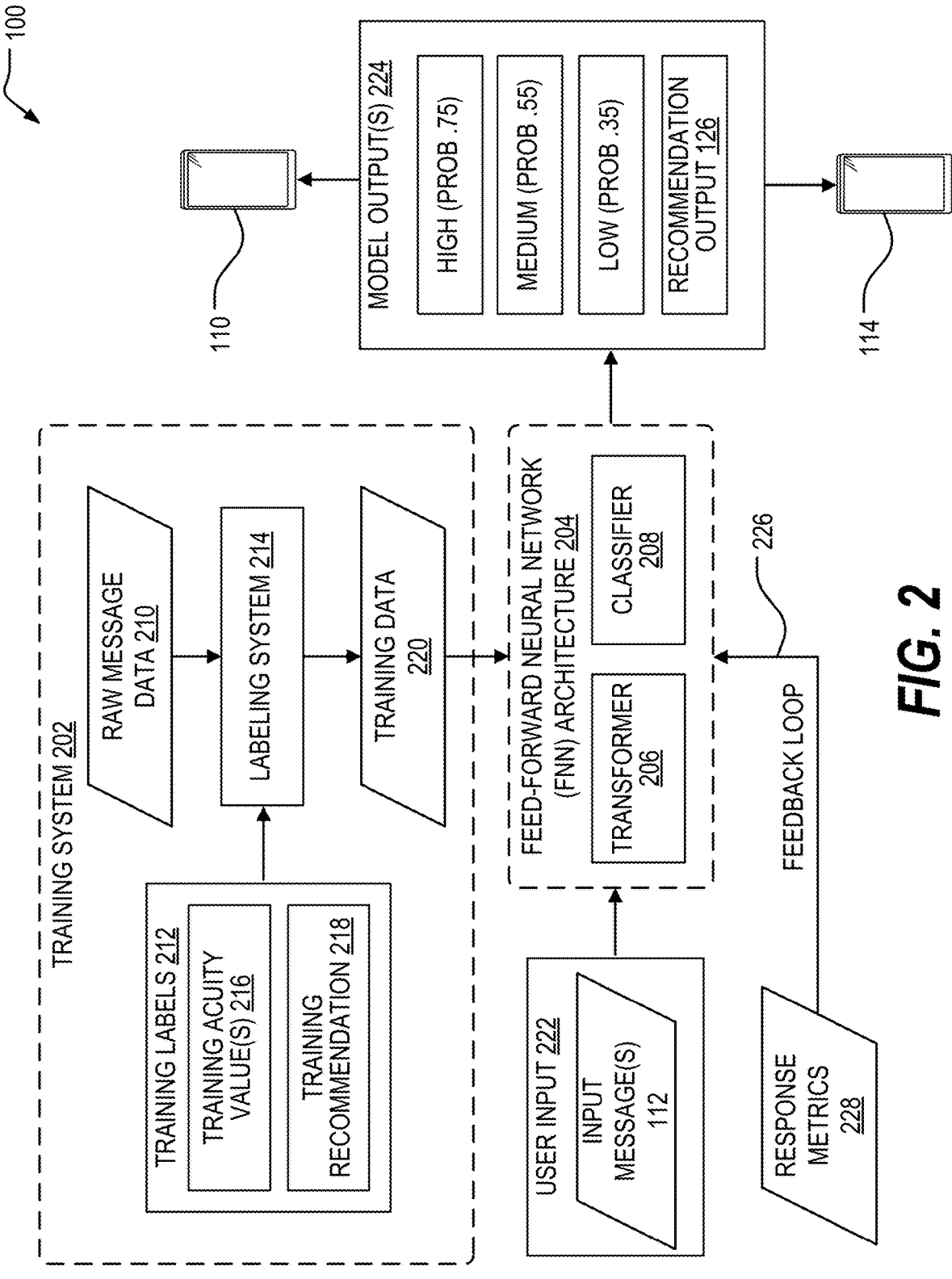
FIG. 2 illustrates an example system including a machine-learning message control platform having a training system for a neural network architecture, which can form at least a part of the system depicted in FIG. 1, in accordance with some embodiments discussed herein.

FIG. 2 illustrates an example system 100 including a message control platform 102 with a training system 202 for a machine learning architecture, such as a feed-forward neural network (FNN) architecture 204. The FNN architecture 204 may be provided on various types of hardware, including graphics processing units, tensor processing units, central processing units, high-speed interconnects, and other processing units.

In some embodiments, the training system 202 can perform one or more training procedures for the FNN architecture 204, which can involve training a transformer model 206 (e.g., a Decoding-enhanced Bi-directional Encoder Representations (DeBERTa) model) alongside a classifier 208. The classifier 208 can include multiple classification layers added to the FNN architecture 204. To train these components of the FNN architecture 204, raw message data 210 including a dataset of a plurality of text messages can be labeled via a supervised learning procedure. For instance, during the supervised machine-learning operation, the data set can be modified with training labels 212, which are assigned to the individual text messages. A labeling system 214 can receive the training labels 212 via a manual input from a doctor, nurse, or other qualified training personnel engaging in the training operation. The training labels 212 can include a training acuity value 216 (e.g., a rank between 1-3, 1-5, 1-10, or 1-100, a "low," "medium," or "high" value, and so forth) associated with the patient information conveyed by the raw message data 210. These training acuity values 216 can be assessed by the FNN architecture 204 to train the message prioritization system 106. In some embodiments, dozens or even hundreds or thousands of training labels 212 can be applied to text messages of the raw message data 210 during a model training procedure.

Additionally, the training labels 212 can include training recommendations 218 provided to the training system 202 and assigned to individual text messages of the raw message data 210. The training recommendations 218 can include recommendations, in a textual, human-readable descriptive form, for additional actions to be taken by the recipient or drafter of the text message. For instance, the training recommendation 218 can include a recommendation to contact another type of doctor (e.g., a cardiologist, a surgeon, etc.), schedule an operation, schedule a consultation, and/or schedule an imaging procedure. The labeling operations disclosed herein can use the training labels 212 to transform the raw message data 210 into training data 220 for the FNN architecture 204. In this way, the computing systems operating the message control platform 102 can do things which surpass previous computing systems.

This approach can cause the model(s) of the message control platform 102 to learn to prioritize nurse paging messages effectively, categorizing them into "High," "Medium," or "Low" acuity classifications based on their respective importance levels. By way of example, a user input 222 at the second computing device 114 can generate input message(s) 112 saying "Patient is experiencing chest pains and is losing consciousness." This input message(s) 112 can be analyzed by the transformer model 206 and the classifier 208 of the FNN architecture 204 to generate one or more model outputs 224, which includes an acuity classification (e.g., "high acuity"). Moreover, responsive to the input message(s) 112, the message control platform 102 can generate, using the recommendation generation system 108, a recommendation output 126 such as "Contact a cardiologist," to be presented at the first computing device 110 and/or the second computing device 114.

Once the FNN architecture 204 training is completed and the message control platform 102 is fine-tuned, the model can predict with high accuracy the "class" of the respective input text (e.g., a high acuity classification, a medium acuity classification, and/or a low acuity classification). The message control platform 102 can also include a customized training procedure which optimizes model parameters according to the custom data generated by the training system 202. Different hospitals and clinics may apply training acuity value 216 in accordance with their patient workflow procedures. Furthermore, once trained, the message control platform's performance can be tested on "test data" to predict their acuity classifications. Ground truth of the test data can be determined by comparing the predicted classes with the actual (e.g., manually annotated classes) to establish an accuracy value.

Additionally, as noted above, the message control platform 102 can provide additional functionality using the recommendation generation system 108. For instance, the recommendation output can include a recommendation to contact another type of doctor (e.g., a cardiologist, a surgeon, etc.), schedule an operation, schedule a consultation, and/or schedule an imaging procedure.

Moreover, the message control platform 102 can have on or more feedback loops 226 for continuous learning and optimization of the FNN architecture 204. For instance, response metrics 228 generated based on response activity can be measured and calculated, and can include one or more of a response content, a response time, an unaddressed message, or a subsequent action (e.g., a test request, a consultation request, and so forth) performed at the first computing device 110 receiving the input message(s) 112. The feedback system 122 can integrate the response metrics 228 representing clinical interactions with the training dataset 220 to provide continuous learning and refinement of the transformer model 206 and/or the classifier 208, and provide further test and verification data. As such, the message control platform 102 can enhance and/or optimizing AI algorithms of the FNN architecture 204 through comprehensive feedback mechanisms. In this way, the systems 100 disclosed herein can remain aligned with the evolving needs and practices of healthcare professionals.

Figure 3B:
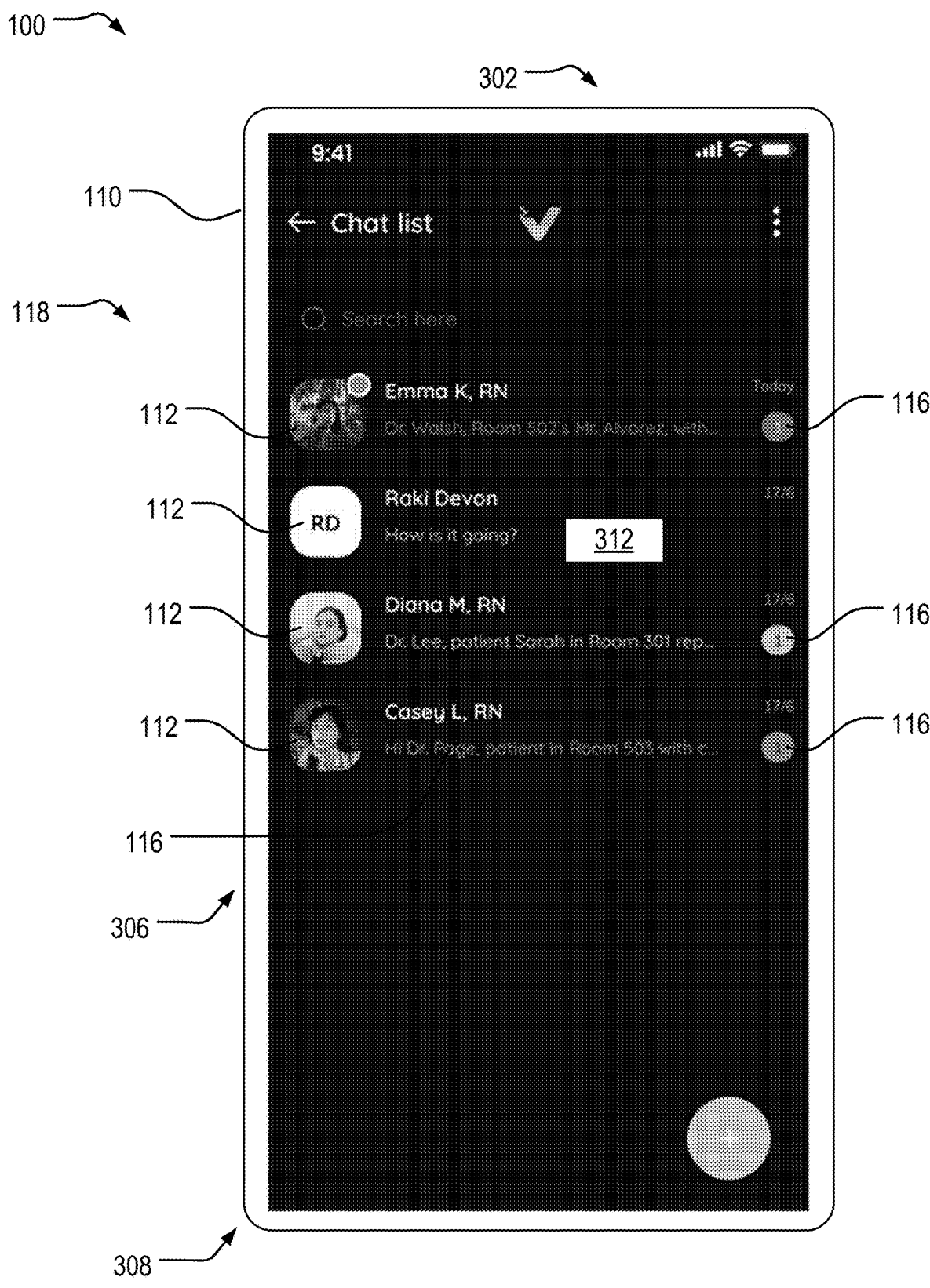
Figure 3C:
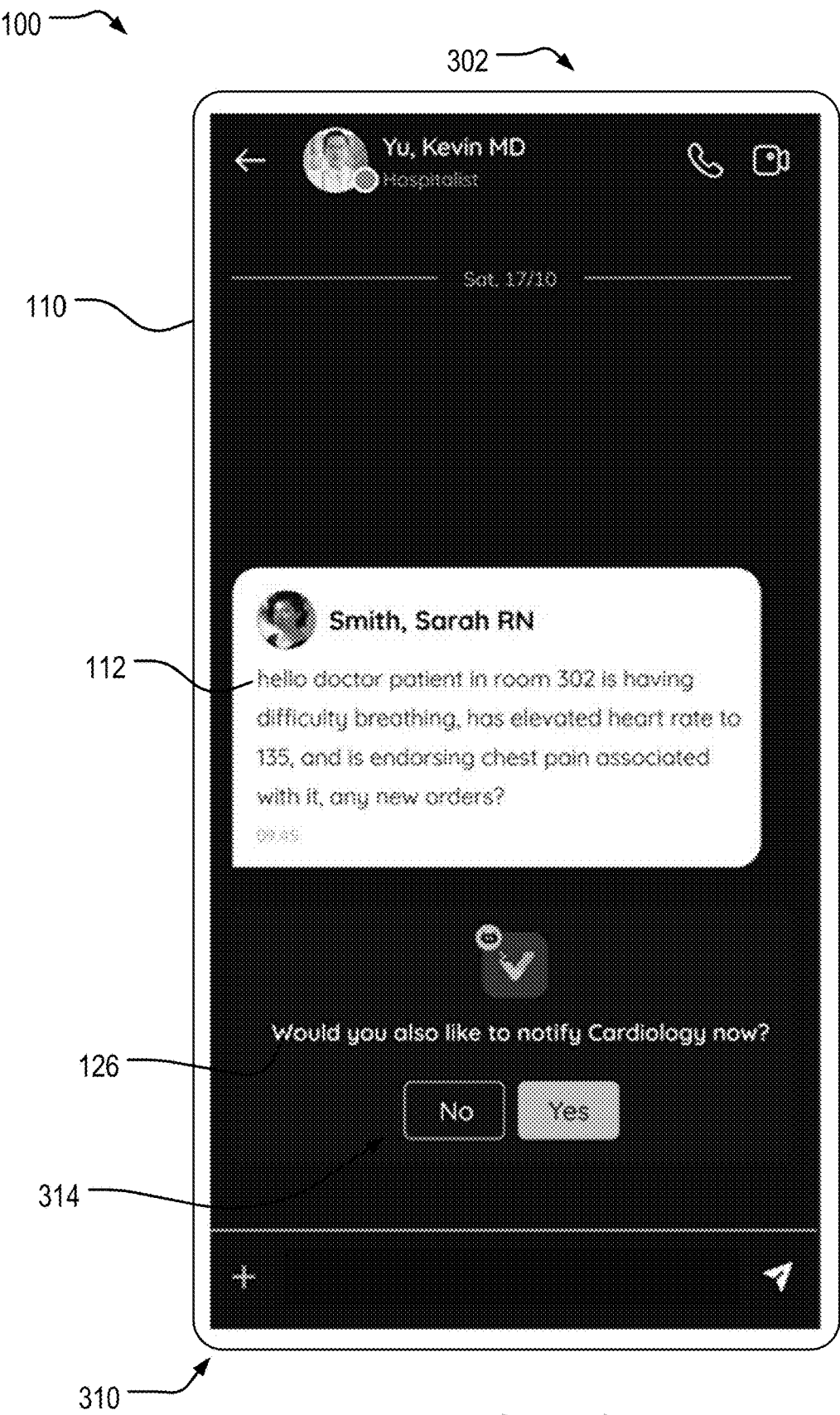
Figure 4:
FIG. 4 illustrates an example system including a machine-learning message control platform implemented using one or more computing devices, which can form at least a part of the system depicted in FIG. 1, in accordance with some embodiments discussed herein.

FIGS. 3A-3C illustrate an example system 100 including one or more graphical user interfaces (GUI) s 302, which can be similar to, identical to, and/or can form at least a portion of the system(s) 100 depicted in FIGS. 1, 2, and 4. FIG. 3A depicts a first GUI 304 including an acuity-based display arrangement 306 of input messages 112 with an acuity-based push notification integration 120. FIG. 3B depicts a second GUI 308 including the acuity-based display arrangement 306 and a plurality of acuity indicators 116 for the input messages 112. FIG. 3C depicts a third GUI 310 including a recommendation output 126 responsive to the input messages 112.

In some embodiments, the first GUI 304 can be presented at the first computing device 110 receiving the input message(s) 112. The first GUI 304 can include a standby interface, an idle interface, a sleep interface, a low power interface, or so forth. Using the acuity-based push notification integration 120, the message control platform 102 can cause the input message(s) 112 to be presented as a list of display messages at the first GUI 304. The plurality of acuity indicator 116 can also be presented at the first GUI 304, for instance, as one or more circles presented next to or below the individual text messages. The acuity indicators 116 can include a number of circles, a color of the circle, a size of the circle, or so forth.

Turning to FIG. 3B, the second GUI 308 can be presented at the first computing device 110 receiving the input message(s) 112 and can include a message drafting interface 312. The message drafting interface 312 can also include the acuity indicator 116 such as a color coding of the text of the messages being presented. Moreover, the second GUI 308 can present the input messages 112 with a display order based on their corresponding acuity classifications. For instance, the highest acuity messages can be presented at a top portion of the message drafting interface 312 and/or lower acuity messages can be presented at a bottom portion of the message drafting interface 312.

Furthermore, FIG. 3C depicts the third GUI 310, which can be presented at the first computing device 110 receiving the input message 112 and/or the second computing device 114 at which the input message 112 is drafted. For instance, the components of the third GUI 310 can be integrated into the message drafting interface 312 at the first computing device 110. The third GUI 310 can include the recommendation output 126, generated by the recommendation generation system 108 upon analyzing the text of the input message 112. The recommendation output 126 can be presented simultaneously with the input message 112 (e.g., above or below the input message 112). Moreover, the recommendation output 126 can be presented with a different style format (e.g., background color, text color, text font, font size, etc.) than the input message 112 to indicate that the recommendation output 126 is not another text message. The recommendation output 126 can include one or more inter-active elements 314 (e.g., icons, buttons, etc.) which, upon receiving a user input, triggers an additional messaging action. For instance, the recommendation output 126 can include a yes or no question (e.g., "Would you like to notify a cardiologist now?"). Receiving a yes input can trigger the message control platform 102 to send a prewritten message to a particular computing device associated with a particular person (e.g., a cariologist, a surgeon, etc.). The pre-written message can be modified with identifying information asso-ciated with the device receiving the yes input such that the recipient of the pre-written message is informed of who originated the pre-written message.

Turning to FIG. 4, an example system 100 can include the computing device 402 to implement the message control platform 102 is disclosed herein. The system 100 depicted in FIG. 4 can be similar to, identical to, or can from at least a portion of the systems 100 discussed above. Additionally, the system 100 can be used to implement any of the methods disclosed herein (e.g., method 500).

In some embodiments, the one or more computing device(s) 402 can include a computer, a personal computer, a desktop computer, a laptop computer 403, a terminal, a workstation, a cellular phone, a mobile device 405 (e.g., a smart mobile device), a tablet, a wearable device (e.g., a smart watch, smart glasses, a smart epidermal device, etc.) a multimedia console, a television, an Internet-of-Things (IoT) device, a smart home device, a medical device, a Virtual Reality (VR) device or headset 407, an augmented reality (AR) device, a vehicle (e.g., a smart bicycle, an automobile computer, etc.), a server device 130, any com-binations thereof, and/or the like. Moreover, the computing device(s) 402 can include the first computing device 110, the second computing device 114 and/or a remote server device 130.

The computing device 402 may be a computing system capable of executing a computer program product (e.g. a computer program code) to perform a computer process. The components of the message control platform 102 (e.g., the message prioritization system 106, the recommendation generation system 108, the feedback system 122, the trans-former model 206, the classifier 208, etc.) can be stored and executed at the computing device(s) 402 (e.g., as one or more software components, algorithm modules, or so forth). Data and program files may be input to the computing device 402 which reads the files and executes the programs therein to provide the various components of the message control platform 102 and generate GUIs 304, 308, and/or 310. Some of the elements of the computing device 402 include one or more hardware processors 404, one or more memory devices 406, and/or one or more ports, such as input/output (IO) port(s) 408 and communication port(s) 410. Various ele-ments of the computing device 402 may communicate with one another by way of the communication port(s) 410 and/or one or more communication buses, point-to-point commu-nication paths, or other communication means.

The processor 404 and other processors described herein may include, for example, a central processing unit (CPU), a microprocessor, a microcontroller, a digital signal proces-sor (DSP), a graphics processing unit (GPU) and/or one or more internal levels of cache. There may be one or more processors 404, such that the processor 404 comprises a single central-processing unit, or a plurality of processing units capable of executing instructions and performing operations in parallel with each other, commonly referred to as a parallel processing environment.

The computing device 402 may be a standalone computer, a distributed computer, or any other type of computer, such as one or more external computers made available via a cloud computing architecture, such as the server devices 130. The presently described technology is optionally imple-mented in software stored on the data storage device(s) such as the memory device(s) 406, and/or communicated via one or more of the ports 408 and 410, thereby transforming the computing device 402 in FIG. 4 into a special purpose machine for implementing the operations of the message control platform 102. Furthermore, various operations of the message control platform 102 herein improve the efficiency of the computing device 402 by optimizing messaging application presentation efficiency. For instance, the tech-niques disclosed herein can require less processing power and/or can reduce memory storage requirements as com-pared to other messaging systems.

The one or more memory device(s) 406 may include any non-volatile data storage device capable of storing data generated or employed within the computing device 402, such as computer executable instructions for performing a computer process, which may include instructions of both application programs and an OS that manages the various components of the computing device 402. The memory device(s) 406 may include, without limitation, magnetic disk drives, optical disk drives, solid state drives (SSDs), flash drives, and the like. The memory device(s) 406 may include removable data storage media, non-removable data storage media, and/or external storage devices made available via a wired or wireless network architecture with such computer program products (e.g., computer program code), including one or more database management products, web server products, application server products, and/or other addi-tional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory device(s) 406 may include volatile memory (e.g., dynamic random-access memory (DRAM), static ran-dom-access memory (SRAM), etc.) and/or non-volatile memory (e.g., read-only memory (ROM), flash memory, etc.).

Computer program products (e.g., computer program code) containing mechanisms to effectuate the systems and methods in accordance with the presently described tech-nology may reside in the memory device(s) 406 which may be referred to as machine-readable media. It will be appre-ciated that machine-readable media may include any tan-gible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computing device 402 includes one or more ports, such as the I/O port 408 and the communication port 410, for communicating with other computing, network, or vehicle devices. It will be appreci-ated that the I/O port 408 and the communication port 410 may be combined or separate and that more or fewer ports may be included in the computing device 402.

The I/O port 408 may be connected to an I/O device, or other device, by which information is input to or output from the computing device 402. Such I/O devices may include one or more input devices, output devices, and/or environment transducer devices.

In one implementation, the input devices convert a human-generated signal, such as, human voice, physical movement, physical touch or pressure, and/or the like, into electrical signals as input data into the computing device 402 via the I/O port 408. Similarly, the output devices may convert electrical signals received from the computing device 402 via the I/O port 408 into signals that may be sensed as output by a human, such as sound, light, and/or touch. The input device may be an alphanumeric input device, including alphanumeric and other keys for communicating information and/or command selections to the processor 404 via the I/O port 408. The input device may be another type of user input device including, but not limited to direction and selection control devices, such as a mouse, a trackball, cursor direction keys, a joystick, and/or a wheel; one or more sensors, such as a camera, a microphone, a positional sensor, an orientation sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touch-screen.

Furthermore, in some implementations, the communication port 410 is connected to a network and the computing device 402 may receive network data useful in executing the methods and systems set out herein as well as transmitting information and network configuration changes determined thereby. Stated differently, the communication port 410 can connect the computing device 402 to one or more communication interface devices configured to transmit and/or receive information between the computing device 402 and other devices by way of one or more wired or wireless communication networks 128 or connections. Examples of such network connections can include, without limitation, Universal Serial Bus (USB), Ethernet, Wi-Fi, Bluetooth®, Near Field Communication (NFC), and so on. One or more such communication interface devices may be utilized via the communication port 410 to communicate one or more other machines, either directly over a point-to-point communication path, over a wide area network (WAN) (e.g., the Internet), over a local area network (LAN), over a cellular network (e.g., third generation (3G), fourth generation (4G), Long-Term Evolution (LTE), fifth generation (5G), etc.) or over another communication means. Further, the communication port 410 may communicate with an antenna or other link for electromagnetic signal transmission and/or reception.

Turning to FIG. 5, an example method 500 of controlling messages with a machine-learning message control platform is depicted. The method 500 can be performed by the system(s) and device(s) discussed above regarding FIGS. 1-4.

In some embodiments, at operation 502, a text message of a plurality of text messages is received, and the text message includes patient-related data. The text message may be received at a computing device in some embodiments.

At operation 504, an acuity indicator is presented. The acuity indicator may be presented at a display screen of the computing device. The acuity indicator may have been generated by a message prioritization system of the machine-learning message control platform. The acuity indicator may correspond to the patient-related data and may indicate an acuity classification of the patient-related data.

At operation 506, the plurality of text messages are presented with an acuity-based display arrangement. The plurality of text messages may be presented at the display screen of the computing device. The acuity-based display arrangement may describe presentation prominence for the plurality of text messages using a plurality of acuity classifications generated by the message prioritization system of the machine-learning message control platform.

The method 500 can also include operations 508-514. At operation 508, a recommendation output message may be generated. The recommendation output message may be generated using a recommendation generator system of the machine-learning message control platform. At operation 509, the recommendation output message may be sent to another device (e.g., a computing device). For example, the recommendation output message may be sent to a computing device for presentation at a user interface on that computing device. At operation 510, a response metric may be generated. The response metric may be generated by measuring a characteristic of an activity performed at the computing device responsive to the text message. At operation 512, the response metric may be provided to the message prioritization system. At operation 514, the message prioritization system may be optimized by using the response metric as feedback.

It is to be understood that the specific order or hierarchy of operations in the method(s) depicted in FIG. 5 and throughout this disclosure are instances of example approaches and can be rearranged while remaining within the disclosed subject matter. For instance, any of the operations depicted in FIG. 5 and throughout this disclosure may be omitted, repeated, performed in parallel, performed in a different order, and/or combined with any other of the operations depicted in FIG. 5 and throughout this disclosure.

FIG. 6 illustrates an example system 600 comprising a plurality of decoders that may be used to facilitate machine learning processes described herein. The system 600 comprises a number n of decoders, with a first decoder 602A, a second decoder 602B, and a final decoder 602N being shown. In some embodiments, decoder systems may include only one decoder, and other decoders illustrated in system 600 may be omitted in these systems. In other embodiments, any number of decoders may be included. The contents of the first decoder 602A are illustrated in detail, but other decoders (e.g., second decoder 602B, final decoder 602N) may include the same or similar components in some embodiments.

The first decoder 602A includes a self-attention unit 604, a first normalization unit 606, an encoder-decoder attention unit 608, a second normalization unit 610, first and second feed-forward layers 612A, 612B, and a third normalization unit 614. Each of these components within the first decoder 602A are discussed herein in turn.

The system 600 may receive input material 601, with the input material 601 being received at the self-attention unit 604 of the first decoder 602A. However, the system 600 may receive the input material 601 at another component in other embodiments. The input material 601 may include the primary material that is being analyzed by the model. However, the input material 601 may also include other material received from various sources to improve the quality of the model that is developed. For example, input material 601 may include additional contextual material in the form of census data, health data, financial data, etc. from various websites, databases, servers, etc. In some embodiments, contextual data and other data may be obtained through the use of web crawling and/or other techniques. In obtaining data, systems may focus on obtaining data from trustworthy or authoritative sources. Specialized data sets may also be obtained from other sources. Furthermore, input material 601 may include input prompts that help to guide models. In some embodiments, systems may avoid utilizing confidential health data or protected health information (PHI) unless the data or information has been aggregated and anonymized or the data or information is being used with the consent of the relevant individuals.

The self-attention unit 604 may comprise a self-attention mechanism and/or one or more self-attention layers in some embodiments. Self-attention unit 604 and/or attention unit 608 may be multi-headed attention mechanisms in some embodiments that may enable models to focus on different aspects of an input sequence simultaneously so that an improved contextual understanding may be provided. Multi-headed attention mechanisms may be beneficial to determine a base model that is used. With multi-headed attention mechanisms, patients may have multiple levels of acuity that may change rapidly. Also, with multi-headed attention mechanisms, words within an input may be interpreted under multiple definitions as opposed to other approaches where every word has a singular definition.

The self-attention unit 604 may perform various tasks related to self-attention. The self-attention unit 604 may enable models to weigh different parts of an input sequence when processing elements, thereby allowing other portions of the first decoder 602A to focus on the most relevant parts of the input material 601. The self-attention unit 604 may enable models to determine the importance of different elements that are received at the system 600. For example, where the input material 601 is a large amount of text, the self-attention unit 604 may be configured to determine the relative importance of certain words, clauses, sentences, or other portions of the text. However, even where the input material 601 is provided in some other form, the self-attention unit 604 may be configured to determine the relative importance of other aspects (e.g., tokens) of the input material 601. The self-attention unit 604 may be used to effectively capture dependencies (e.g., long-term dependencies) in sequential data. In some embodiments, the self-attention unit 604 may enable inputs to interact with each other. The self-attention unit 604 may allow for parallel computation at once, thereby making self-attention efficient when dealing with a large time series. Furthermore, self-attention units 604 may determine the importance of different aspects of the input material 601 based on their relationship with other aspects of the input material 601, and the importance of each aspect may be determined based on a thorough examination of these relationships and the overall context. In some embodiments, self-attention units 604 may assign a quantifiable value or score for the importance of an aspect of the input material 601.

Material (e.g., data) may be output from the self-attention unit 604 to the first normalization unit 606. The normalization units 606, 610, 614 may perform various normalization techniques to data. Normalization performed at the normalization units may improve the consistency of any resulting models. Normalization may also make models that are generated more comparable—with normalization providing greater consistency in various aspects of the models, the models may be more easily compared to understand their differences. Normalization may enable statistical analysis to be more easily conducted. Normalization may also rescale certain features to a common range. For example, where scores have been obtained for the importance of certain aspects of the input material 601 at the self-attention unit 604, the first normalization unit 606 may normalize these scores so that highest scoring feature is assigned a certain value (e.g., 1) and the lowest scoring feature is assigned another value (e.g., 0). Normalization may also be beneficial when different features are being scored on different scales.

Material may be output from the first normalization unit 606 to the attention unit 608. The attention unit 608 may be configured to perform one or more attention techniques. The attention unit 608 may allow the first decoder 608 to focus on specific aspects of input material 601 during the learning process. The attention unit 608 may focus on the aspects of input material 601 that have been determined to be the most important (e.g., those with the highest scores) by other components of the first decoder 602A in some embodiments. The attention unit 608 may enhance the quality of any models generated by the first decoder 602A. Material may be output from the attention unit 608 to the second normalization unit 610 for further normalization.

Material may be output from the second normalization unit 610 to the feed-forward neural networks 612A, 612B. While two feed-forward neural networks 612A, 612B are illustrated in the first decoder 602A, a different number of feed-forward neural networks may be included in a particular decoder in other embodiments. The feed-forward neural networks 612A, 612B and other feed-forward neural networks may be implemented on a processing unit or a processor in some embodiments. While feed-forward neural networks 612A, 612B are illustrated in the first decoder 602A, other types of artificial neural networks may be used in decoders in other embodiments. For example, convolutional neural networks (CNNs), recurrent neural networks (RNNs), long short-term memory (LSTM) networks, gated recurrent units (GRUs), autoencoders, generative adversarial networks (GANs), transformers, and the like may be used. The feed-forward neural networks 612A, 612B may be configured to receive data from previous units at an input layer. The input layer may comprise a plurality of neurons, with each neuron representing a particular aspect from the input material 601. The feed-forward neural networks 612A, 612B may also comprise an output layer that provides an output, which may be in the form of a prediction. One or more hidden layers may be positioned between the input layer and the output layer of the feed-forward neural networks 612A, 612B. Any number of hidden layers may be included in the feed-forward neural networks 612A, 612B. The hidden layers may be configured to learn complex patterns within the data. The hidden layers may each comprise a plurality of neurons, with each neuron applying a weighed sum of inputs followed by an activation function. Information May flow through the feed-forward neural networks 612A, 612B in one direction, with the information flowing from the input layer towards the output layer.

Material may be output from the feed-forward neural networks 612A, 612B to the third normalization unit 614 for further normalization. Material may be output from the third normalization unit 614 to other decoders 602B, 602N. Material output from the decoders may be output to the human feedback unit 615 in some embodiments. The human feedback unit 615 may be configured to enable human-in-the-loop feedback approaches described herein to be implemented. The human feedback unit 615 may comprise an interface through which an expert, healthcare provider, or another individual may review various features of the model and make any adjustments that may be necessary or desired.

Material from the human feedback unit 615 may be output to the linearization unit 616, alternatively, where no human feedback unit 615 is used, material from the final decoder 602N may be output to the linearization unit 616. The linearization unit 616 may be configured to perform linearization on material that it receives. Linearization may result in a transformation of complex and/or non-linear relationships or representations or sequences into a linear form that may be processed more efficiently by other parts of a decoder.

Material output from the linearization unit 616 may be output to the Softmax unit 618. The Softmax unit 618 may be configured to scale logits into a particular range. Logits may be raw output values received from other portions of the system 600. The Softmax unit 618 may use a Softmax function to complete scaling. Softmax is an activation function that may convert the logits into a probability distribution, scaling the logits into a range between 0 and 1 where the sum of all outputs probabilities is equal to 1. The material output from the Softmax unit 618 may serve as the output of the overall system 600, but further processing may be performed on this material in other embodiments.

Figure 7:
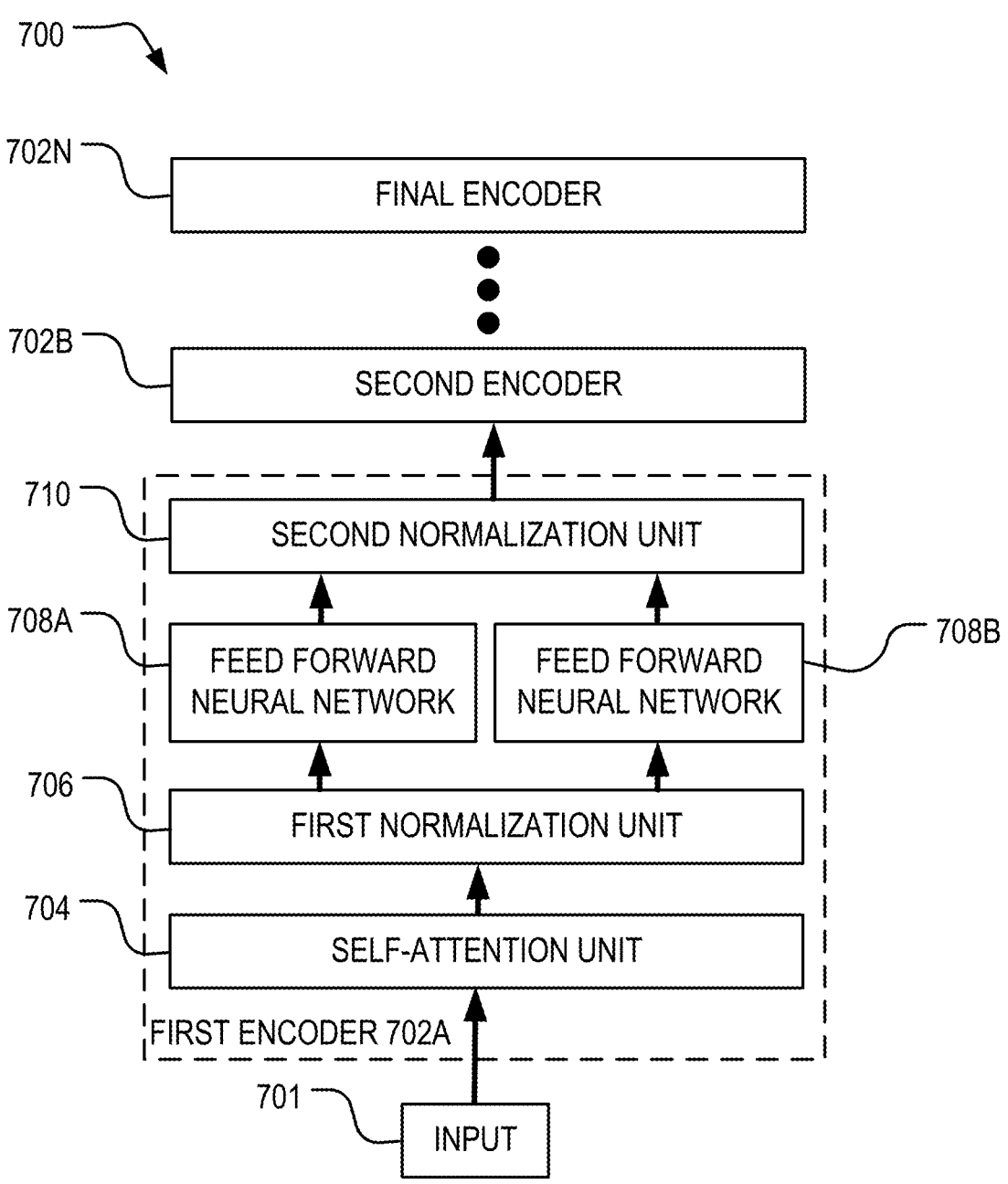
FIG. 7 illustrates an example system comprising a plurality of encoders that may be used to facilitate machine learning processes described herein, in accordance with some embodiments discussed herein.
Figure 8:
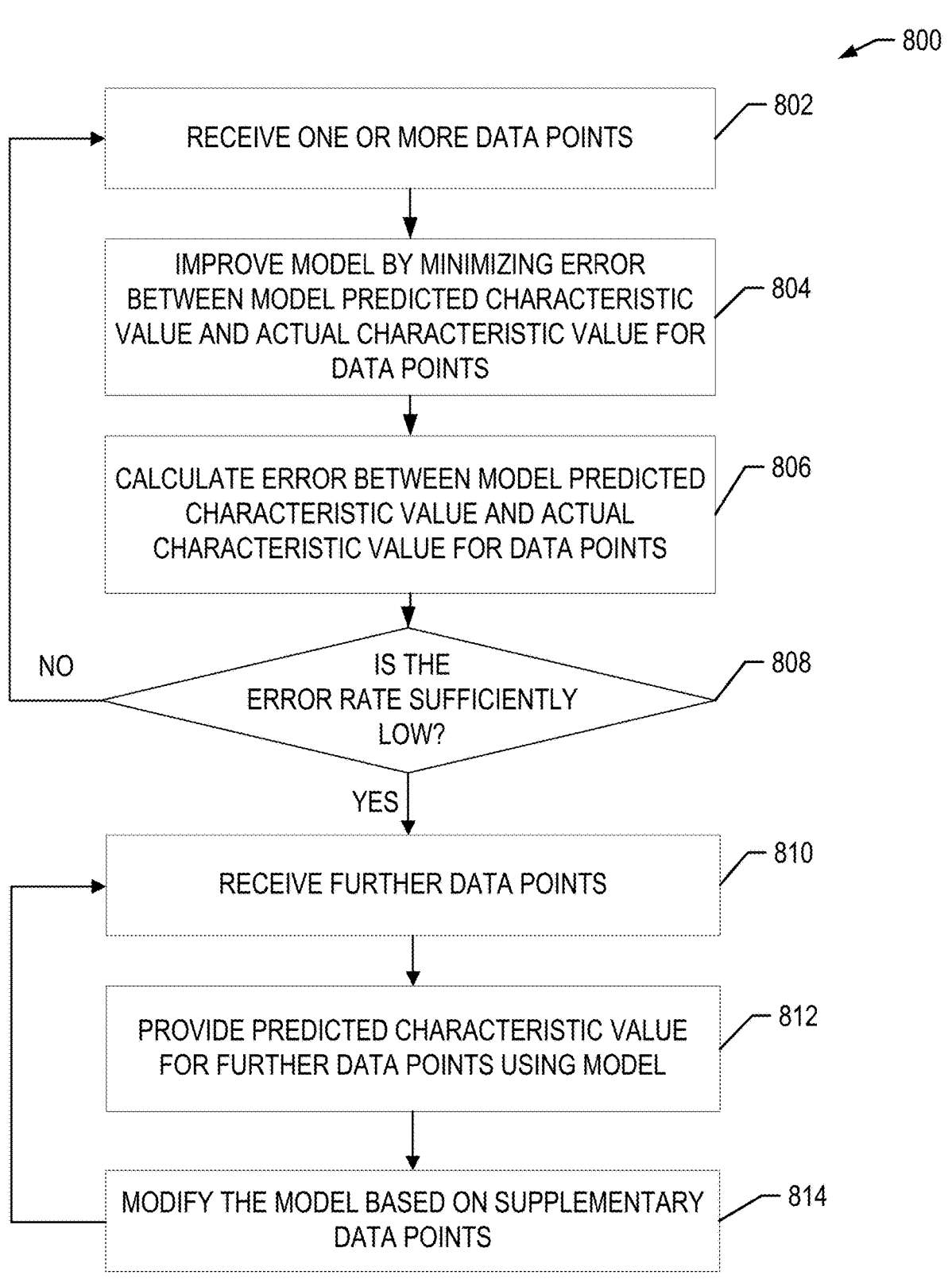
FIG. 8 is a flowchart of an example method of machine learning, such as may be utilized with artificial intelligence, in accordance with an embodiment of the present invention.

FIG. 7 illustrates an example system 700 comprising a plurality of encoders that may be used to facilitate machine learning processes described herein. The system 700 comprises a number n of encoders, with a first encoder 702A, a second encoder 702B, and a final encoder 702N being shown. In some embodiments, encoder systems may include only one encoder, and other encoder illustrated in system 700 may be omitted in these systems. In other embodiments, any number of encoders may be included. The contents of the first encoder 702A are illustrated in detail, but other decoders (e.g., second decoder 702B, final decoder 702N) may include the same or similar components in some embodiments.

Input material 701 may be received in the system 700 at the self-attention unit 704 of the first encoder 702A. The self-attention unit 704 may be similar to the self-attention unit 604 discussed in reference to FIG. 6. Material output from the self-attention unit 704 may be output to the first normalization unit 706. The first normalization unit 706 and second normalization unit 710 may both be similar to the normalization units 606, 610, 614 discussed in reference to FIG. 6. Material output from the first normalization unit 706 may be output to the feed-forward neural networks 708A, 708B. Feed-forward neural networks 708A, 708B may be similar to the feed-forward neural networks 612A, 612B discussed in reference to FIG. 6. While two feed-forward neural networks 708A, 708B are illustrated in the first encoder 702A, any number of feed-forward neural networks may be used in other embodiments. Material output from the feed-forward neural networks 708A, 708B may be output to the second normalization unit 710. Material output from the second normalization unit 710 may be output to the second encoder 702B. Material output from the second encoder 702B may be output to other encoders up to the final encoder 702N.

While the system 600 of FIG. 6 relies upon decoders and the system 700 of FIG. 7 relies upon encoders, these systems 600, 700 may be combined together in some embodiments to form a system using both decoders and encoders in some embodiments. Alternatively, other systems may be created using both decoders and encoders. However, decoder-only or auto-regressive models or systems like those illustrated in system 600 may be used, and this may be beneficial to enhance the efficiency of the system. In some embodiments, an encoder system comprising one or more encoders may be used to process inputs and to compress the inputs into a representation in latent space, and a decoder system comprising one or more decoders may be used to take the representation and generate a particular output sequence.

Additionally, in some embodiments, refinement of models may optionally be validated by healthcare professionals, subject matter experts, or others, providing a human-in-the-loop feedback approach. With this approach, the clinical accuracy and trustworthiness of any developed models may be enhanced. Human-in-the-loop feedback approaches may be implemented through supervised fine tuning (SFT), reinforcement learning through human feedback (RLHF), and/or other techniques. In some embodiments, human-in-the-loop feedback approaches may occur regularly or effectively in real-time as models are being developed, but this feedback may additionally or alternatively be provided as part of a more detailed review occurring on a less frequent basis (e.g., a quarterly review of models to confirm their accuracy and whether further room for optimization exists). Human-in-the-loop feedback approaches may also be performed through survey based review, metric based review (e.g., based on throughput), or through other approaches.

In some embodiments, artificial intelligence and machine learning may be used to generate models to predict data that may be used for various tasks. FIG. 10 is a flowchart of an example method 800 of machine learning, such as may be utilized with artificial intelligence for various embodiments of the present invention. At least one processor or another suitable device may be configured to develop a model, such as described herein in various embodiments. In this regard, the developed model may be deployed and utilized to predict data that may be used in any of the applications described herein.

In some systems, even after the model is deployed, the systems may beneficially improve the developed model by analyzing further data points. By utilizing artificial intelligence, a novice user may benefit from the experience of the models utilized. Even the most experienced users may benefit from the use of the systems—by using a model generated through artificial intelligence, complex estimations and computations may be made that the user could not otherwise make on their own.

By receiving several different types of data, the example method 800 may be performed to generate complex models. The example method 800 may find relationships between different types of data that may not have been anticipated. By detecting relationships between different types of data, the method 800 may generate accurate models even where a limited amount of data is available.

In some embodiments, the model may be continuously improved even after the model has been deployed. Thus, the model may be continuously refined based on changes over time, which provides a benefit as compared with other models that stay the same after being deployed. The example method 800 may also refine the deployed model to fine-tune weights that are provided to various types of data based on subtle changes. Where changes have occurred, the method 800 may continuously refine a deployed model to quickly account for the changes and provide a revised model that is accurate. By contrast, where a model is not continuously refined, changes in context, an environment, etc. may make the model inaccurate until a new model may be developed and implemented, and implementation of a new model may be very costly, time-consuming, and less accurate than a continuously refined model.

At operation 802, one or more data points are received. These data points may or may not be the initial data points being received. These data points preferably comprise known data on a characteristic value (i.e. the characteristic that the model may be used to predict). The data points provided at operation 802 are preferably historical data points with verified values to ensure that the model generated is accurate. The data points may take the form of discrete data points. However, where the data points are not known at a high confidence level, a calculated data value may be provided, and, in some embodiments, a standard deviation or uncertainty value may also be provided to assist in determining the weight to be provided to the data value in generating a model. In this regard, the predicted characteristic value may be formed based on historical comparisons of the characteristic value and/or other data.

At operation 804, a model is improved by minimizing error between a predicted characteristic value generated by the model and an actual characteristic value for data points. In some embodiments, an initial model may be provided or selected by a user. The user may provide a hypothesis for an initial model, and the method 800 may improve the initial model. However, in other embodiments, the user may not provide an initial model, and the method 800 may develop the initial model at operation 804, such as during the first iteration of the method 800. The process of minimizing error may be similar to a linear regression analysis on a larger scale where three or more different variables are being analyzed, and various weights may be provided for the variables to develop a model with the highest accuracy possible. Where a certain variable has a high correlation with the characteristic value, that variable may be given increased weight in the model. In refining the model by minimizing the error between the predicted characteristic value generated by the model and the actual or known characteristic value, the component performing the method 800 may perform a very large number of complex computations. Sufficient refinement results in a more accurate model.

In some embodiments, the accuracy of the model may be checked. For example, at operation 806, the accuracy of the model is determined. This may be done by calculating the error between the model predicted characteristic value generated by the model and the actual characteristic value from the data points. In some embodiments, error may also be calculated before operation 804. By calculating the accuracy or the error, the method 800 may determine if the model needs to be refined further or if the model is ready to be deployed. Where the characteristic value is a qualitative value or a categorical value, the accuracy may be assessed based on the number of times the predicted value was correct. Where the characteristic value is a quantitative value, the accuracy may be assessed based on the difference between the actual value and the predicted value.

At operation 808, a determination is made as to whether the calculated error is sufficiently low. A specific threshold value may be provided in some embodiments. The threshold value may be altered by the user in some embodiments. If the error rate is not sufficiently low, then the method 800 may proceed back to operation 802 so that one or more additional data points may be received. If the error rate is sufficiently low, then the method 800 proceeds to operation 810. Once the error rate is sufficiently low, the training phase for developing the model may be completed, and the implementation phase may begin where the model may be deployed to predict characteristic values.

By completing operations 802, 804, 806, and 808, a model may be refined through machine learning utilizing artificial intelligence based on the historical comparisons of a characteristic value with other data and based on known deviations of the characteristic value for the historical comparisons. Notably, example model generation and/or refinement may be accomplished even if the order of these operations is changed, if some operations are removed, or if other operations are added.

During the implementation phase, the model may be utilized to provide a determined characteristic value. An example implementation of a model is illustrated from operations 810-812. In some embodiments, the model may be modified (e.g., further refined) based on the received data points, such as at operation 814.

At operation 810, further data points are received. For these further data points, the actual characteristic value may not be known. At operation 812, the model may be used to provide a predicted characteristic value for the further data points. Thus, the model may be utilized to determine the characteristic value.

At operation 814, the model may be modified based on supplementary data points, such as those received during operation 810 and/or other data points. By providing supplementary data points, the model may continuously be improved even after the model has been deployed. The supplementary data points may be the further data points received at operation 810, or the supplementary data points may be provided to the processor from some other source. In some embodiments, the processor(s) or other component performing the method 800 may receive additional data from secondary devices and verify the further data points received at operation 810 using this additional data. By doing this, the method 800 may prevent errors in the further data points from negatively impacting the accuracy of the model.

In some embodiments, supplementary data points are provided to the processor from some other source and are utilized to improve the model. These supplementary data points may be verified before being provided to improve the model, or processor may verify the supplementary data points utilizing additional data.

As indicated above, in some embodiments, operation 814 is not performed and the method proceeds from operation 812 back to operation 810. In other embodiments, operation 814 occurs before operation 812 or simultaneously with operation 812. Upon completion, the method 800 may return to operation 810 and proceed on to the subsequent operations. Supplementary data points may be the further data points received at operation 810 or some other data points.

Various embodiments described herein may related to machine learning techniques and/or models. Machine learning techniques may process and analyze data to enable computer systems to autonomously learn and improve their performance over time from the data, to automatically identify patterns, extract insights, and make informed decisions or predictions without explicit programming for each scenario. The machine learning techniques may include a variety of models or algorithms, including supervised learning techniques, unsupervised learning techniques, reinforcement learning techniques, knowledge-based learning techniques, natural-language-based learning techniques such as natural language generation, natural language processing (NLP) and named entity recognition (NER), deep learning techniques, and the like. The machine learning techniques may be trained using training data. The training data may be used to modify and fine-tune any weights associated with the machine learning models, as well as record ground truth for where correct answers may be found within the data. As such, the better the training data, the more accurate and effective the machine learning model may be. Machine learning models may utilize statistical methods and optimization processes and techniques to adaptively refine their internal parameters, allowing them to generalize from past observations and efficiently solve complex tasks, including classification, regression, clustering, and more. The models may include supervised learning models (e.g., linear regression models, logistic regression models, decision tree models, random forest models, support vector models, neural network models), unsupervised learning models (e.g., K-Means clustering models, hierarchical clustering models, principal component analysis (PCA) models, gaussian mixture models (GMM)), semi-supervised learning models (e.g., a combination of supervised and unsupervised learning approaches where the model is trained on a partially labeled dataset), reinforcement learning models (e.g., agents and Q-learning and deep Q networks (DQNs)), deep learning models (e.g., neural networks), transfer learning models, ensemble learning models, on-line learning models, and instance-based learning models. The supervised learning models may be trained on labeled datasets to learn to map input data to desired output data or labels. This type of learning model may involve tasks like classification and regression. The unsupervised learning model involves models that analyze and identify patterns in unlabeled data. Clustering and dimensionality reduction are common tasks in unsupervised learning. The semi-supervised learning models combine elements of both supervised and unsupervised learning models, utilizing limited labeled data alongside larger amounts of unlabeled data to improve model performance. The reinforcement learning model involves training models to make sequential decisions by interacting with a selected environment. The models may learn through trial and error, receiving feedback in the form of rewards or penalties. The deep learning models may utilize neural networks with multiple layers to automatically learn hierarchical features from data. The neural networks may include interconnected nodes, or "neurons," organized into layers. Each connection between neurons may be assigned a weight that determines the strength of the signal being transmitted. By adjusting the weights based on input data and desired outcomes, neural networks may learn complex patterns and relationships within the data. The neural networks may include an artificial neural networks (ANN), feedforward neural networks (FNNs), convolutional neural networks (CNNs), recurrent neural networks (RNNs), long short-term memory (LSTM) networks, gated recurrent units (GRUs), autoencoders, generative adversarial networks (GANs), transformers, and the like.

The transformer type model or architecture may be configured to process sequences of data, making the model particularly suitable for tasks involving natural language processing (NLP) or benefit from the processing using NLP. The transformer model may include a number of primary elements or components, including input embeddings, encoder and decoder stacks, self-attention and multi-head attention mechanisms, positional encoders, feedforward neural networks, normalization and residual connections, one or more output linear layers, and the like. However, as discussed herein, transformer models may only include decoders without any encoders in some embodiments. During processing, input sequence may be divided into individual tokens, which may be words, sub words, or characters, based on the input data, which may include textual data.

The input embeddings are an input sequence that is transformed into a series of embeddings, where each token is represented as and is mapped to a high-dimensional embedding vector, which captures positional information and the semantic meaning of the token. The embeddings may be a combination of learned token embeddings and positional encodings.

The model may also include an output layer that generates the final predictions or outputs based on the representations generated by the decoder stack. In selected types of tasks (e.g., machine translation), the output layer may produce a probability distribution over a target vocabulary for each position in the output sequence. The transformer components cooperate or work together to capture long-range dependencies, effectively process sequential data, and easily perform processing tasks.

The transformer type machine learning model may involve training a model on one task and transferring the learned knowledge to a related task, often enhancing efficiency and performance. The model may be configured as an ensemble learning model that combines multiple models to make more accurate predictions.

The machine-learning processes as described herein may also be used to generate machine-learning models. A machine-learning model or model, as used herein, is a mathematical representation of a relationship between inputs and outputs, as generated using any machine-learning process including without limitation any process as described above and stored in memory. An input may be submitted to a machine-learning model once created, which generates an output based on the relationship that was derived. For example, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Various embodiments described herein may utilize large language models (LLMs). The LLMs may be configured to understand and generate human language by learning patterns and relationships from vast amounts of input textual data. The model configuration may include setting selected hyperparameters, including the number of layers, hidden units per layer, attention mechanisms, and other architectural details. The LLMs may utilize deep learning techniques to process and generate text. The models may be pre-trained and trained on massive data corpora (e.g., text corpora, image corpora, and the like) and may perform tasks such as text generation, language translation, text summarization, image generation, sentiment analysis, and the like. The LLMs may include, by simple way of example, generative artificial intelligence (AI) or machine learning models. The generative artificial intelligence (AI) model refers to a computational system designed to create new and original data based on patterns and information learned from existing datasets. The generative AI model may employ selected machine learning techniques to generate content, such as text, images, audio, or other forms of media or data, that closely resembles the input data but is not an exact replication. The generative AI models may leverage neural networks and probabilistic methods to produce outputs that exhibit creativity and diversity while maintaining coherence with the input data distribution. The large language models may be trained or pre-trained, and the training and pre-training may involve a combination of data collection, data pre-processing, model architecture design, and optimization.

However, embodiments may use small language models (SLMs) in addition to or as an alternative to large language models (LLMs). For example, an SLM may be deployed directly on a user's computing device (e.g., the user's smartphone, tablet, computer, etc.). Any SLMs used on a computing device may be smaller than an LLM. Where SLMs are used on a computing device, this may enable access to the SLMs without an internet connection on the computing device.

While the presently disclosed technology has been described with reference to various implementations, it will be understood that these implementations are illustrative and that the scope of the presently disclosed technology is not limited to them. Many variations, modifications, additions, and improvements are possible. More generally, implementations in accordance with the presently disclosed technology have been described in the context of particular implementations. Yet, the embodiments described herein may be provided in various contexts. For example, while many embodiments described herein have been described in the context of healthcare, embodiments may be used in other fields (e.g., to provide improved messaging interfaces in schools, businesses, etc.). Functionality may be separated or combined differently in various implementations of the disclosure or described with different terminology. These and other variations, modifications, additions, and improvements may fall within the scope of the disclosure.

What is claimed is:

1. A message control system comprising:
a message prioritization system comprising:
    a processing unit comprising one or more processors;
    one or more memory devices comprising computer program code configured, when executed by the one or more processors, to cause the one or more processors to:
    receive training data corresponding to training messages;
    receive assigned acuity levels for the training messages as part of a supervised learning procedure;
    train a machine-learning architecture based on the training data and the assigned acuity levels for the training messages, wherein the machine-learning architecture comprises one or more decoders, wherein each decoder of the one or more decoders comprises a feed-forward neural network comprising an input layer of nodes, one or more intermediate layers, and an output layer comprising one or more output nodes, and wherein the machine-learning architecture does not include any encoders;
    receive patient-related data corresponding to messages;
    input the patient-related data corresponding to the messages into the machine-learning architecture at the input layer of nodes;
    perform computations based on the patient-related data in the one or more intermediate layers;

generate, for the patient-related data for each patient, an acuity indicator corresponding to the patient-related data as an output of the one or more output nodes, wherein the acuity indicator is generated at least partially based on the computations; and
    cause a message notification for each of the messages to be presented on a first user interface of a first computing device in a particular order based on the acuity indicator for each patient,
wherein the acuity indicator represents an urgency level associated with a condition of a patient.

2. The message control system of claim 1, wherein the machine-learning architecture uses autoregressive generation.

3. The message control system of claim 1,
wherein the first computing device is configured to present the acuity indicator with the message notifications at the first user interface of the first computing device.

4. The message control system of claim 1, wherein the computer program code, upon being executed by the one or more processors, causes the one or more processors to:
    generate a recommendation output message,
    wherein the first computing device is configured to present the recommendation output message.

5. The message control system of claim 1, wherein the first computing device comprises computer readable code and one or more processors, the computer readable code of the first computing device comprising an acuity-based push notification integration with the first computing device, and, when the computer readable code of the first computing device is executed by the one or more processors of the first computing device, the acuity-based push notification integration causes a determination of a display order of the message notifications at a display screen of the first computing device.

6. The message control system of claim 5, wherein the computer readable code is configured, when executed by the one or more processors of the first computing device, to cause the one or more processors to:
    receive a response metric; and
    use the response metric as feedback to optimize the message prioritization system,
    wherein the response metric is based on activity at the first computing device responsive to the messages.

7. The message control system of claim 6, wherein the response metric comprises one or more of a response content, a response time, an unaddressed message, or a subsequent action.

8. The message control system of claim 1, wherein the computer readable code is configured, when executed by the one or more processors, to cause the one or more processors to:
    assign a high-acuity classification to a first message of the messages;
    assign a medium-acuity classification or a low-acuity classification to a second message of the messages; and
    cause the first computing device to present an acuity-based display arrangement in which a first message notification associated with the first message is displayed with a higher presentation prominence than a second message notification associated with the second message.

9. The message control system of claim 8, wherein the higher presentation prominence comprises at least one of a higher position on a list, a font change, a larger font size, a screen portion designation, or a presentation color.

10. The message control system of claim 1, wherein the acuity indicator is based on a color scheme which corresponds to a classification performed by the message prioritization system.

11. The message control system of claim 1, wherein the feed-forward neural network comprises a transformer integrated with a classifier.

12. The message control system of claim 11, wherein the transformer and the classifier are trained with training data including a plurality of training text messages including patient information.

13. The message control system of claim 12, wherein each decoder of the one or more decoders comprises an attention mechanism.

14. The message control system of claim 13, wherein the attention mechanism is a multi-headed attention mechanism.

15. The message control system of claim 14, wherein the machine-learning architecture comprises a human feedback unit configured to allow a human operator to make adjustments to a machine learning model.

16. The message control system of claim 15, wherein the machine-learning architecture is configured to be optimized by using one or more feedback loops.

* * * * *